United States Patent
Greenberg et al.

(10) Patent No.: US 9,486,343 B2
(45) Date of Patent: Nov. 8, 2016

(54) PRE-LOADED MULTIPORT DELIVERY DEVICE

(71) Applicants: Cook Medical Technologies LLC, Bloomington, IN (US); The Cleveland Clinic Foundation, Cleveland, OH (US)

(72) Inventors: Roy K. Greenberg, Bratenahl, OH (US); Krasnodar Ivancev, London (GB); David Ernest Hartley, Wannanup (AU); Werner D. Ducke, Queensland (AU); Erik Rasmussen, Slagelse (DK)

(73) Assignees: Cook Medical Technologies LLC, Bloomington, IN (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/263,633

(22) Filed: Apr. 28, 2014

(65) Prior Publication Data

US 2014/0236277 A1    Aug. 21, 2014

Related U.S. Application Data

(63) Continuation of application No. 13/153,753, filed on Jun. 6, 2011, now Pat. No. 8,709,061.

(30) Foreign Application Priority Data

Jun. 15, 2010  (AU) ................................ 2010202487

(51) Int. Cl.
*A61F 2/966*     (2013.01)
*A61F 2/954*     (2013.01)
(Continued)

(52) U.S. Cl.
CPC ................ *A61F 2/954* (2013.01); *A61F 2/07* (2013.01); *A61F 2/856* (2013.01); *A61F 2/95* (2013.01);
(Continued)

(58) Field of Classification Search
CPC .......... A61F 2/95; A61F 2/954; A61F 2/962; A61F 2/966; A61F 2002/9665; A61F 2002/9517
USPC ................................................ 623/1.11–1.12
See application file for complete search history.

(56) References Cited

U.S. PATENT DOCUMENTS 6,827,726 B2   12/2004  Parodi
7,435,253 B1   10/2008  Hartley et al.
(Continued)

FOREIGN PATENT DOCUMENTS

AU         2009200350 B1    7/2009
WO     WO 2007/142962 A2   12/2007
WO     WO 2009/148602 A1   12/2009

OTHER PUBLICATIONS

Search Information Statement for corresponding AU patent application No. 2010202487, dated Apr. 8, 2011, 6 pages.
(Continued)

*Primary Examiner* — Sarah W Aleman
(74) *Attorney, Agent, or Firm* — Brinks Gilson & Lione

(57) ABSTRACT

A pre-loaded stent graft delivery device and stent graft, the stent graft delivery device. The stent graft has at least one fenestration or side arm and the fenestration is preloaded with an indwelling guide wire. Indwelling access sheaths are provided within auxiliary lumens of a pusher catheter and dilators are preloaded into the access sheaths along with the indwelling guide wire. A handle assembly at a distal end of the guide wire catheter. The handle includes a multiport manifold with access ports to the auxiliary lumens in the pusher catheter. Upon deployment of the stent graft into the vasculature of a patient, the indwelling guide wire can be used to facilitate cathertization of a side branch or target vessel through the fenestration or be used to stabilize the access sheath during catheterization, advancement of the access sheath into the target vessel and deployment of a covered or uncovered stent therein through the access sheath.

17 Claims, 12 Drawing Sheets

(51) Int. Cl.
  *A61F 2/07* (2013.01)
  *A61F 2/95* (2013.01)
  *A61F 2/856* (2013.01)
  *A61F 2/958* (2013.01)
  *A61F 2/06* (2013.01)
  *A61F 2/89* (2013.01)

(52) U.S. Cl.
  CPC ............ *A61F 2/958* (2013.01); *A61F 2/966* (2013.01); *A61F 2/89* (2013.01); *A61F 2002/061* (2013.01); *A61F 2002/075* (2013.01); *A61F 2002/9511* (2013.01); *A61F 2002/9517* (2013.01); *A61F 2002/9583* (2013.01); *A61F 2002/9665* (2013.01)

(56) References Cited

U.S. PATENT DOCUMENTS

| | | |
|---|---|---|
| 7,867,270 B2 | 1/2011 | Hartley et al. |
| 2002/0143383 A1 | 10/2002 | Parodi |
| 2003/0181923 A1 | 9/2003 | Vardi |
| 2004/0230287 A1 | 11/2004 | Hartley et al. |
| 2005/0131518 A1 | 6/2005 | Hartley et al. |
| 2007/0043425 A1 | 2/2007 | Hartley et al. |
| 2007/0083215 A1 | 4/2007 | Hamer et al. |
| 2007/0219614 A1 | 9/2007 | Hartley |
| 2007/0219621 A1 | 9/2007 | Hartley et al. |
| 2007/0233220 A1 | 10/2007 | Greenan |
| 2007/0299499 A1 | 12/2007 | Hartley et al. |
| 2008/0109065 A1* | 5/2008 | Bowe ................. A61F 2/95 623/1.13 |
| 2010/0198328 A1 | 8/2010 | Hartley et al. |

OTHER PUBLICATIONS

Examiner's first report for corresponding AU patent application No. 2010202487, dated Apr. 11, 2011, 4 pages.
Examiner's report No. 2 for corresponding AU patent application No. 2010202487, dated Jun. 15, 2011, 3 pages.
Patent Examination Report No. 1 for corresponding AU patent application No. 2011265608, dated Apr. 30, 2014, 4 pages.
International Search Report and Written Opinion for PCT/US2011/039241, dated Dec. 19, 2012, 7 pgs.
International Search Report and Written Opinion for PCT/US2011/039241, dated Oct. 7, 2011, 12 pgs.

* cited by examiner

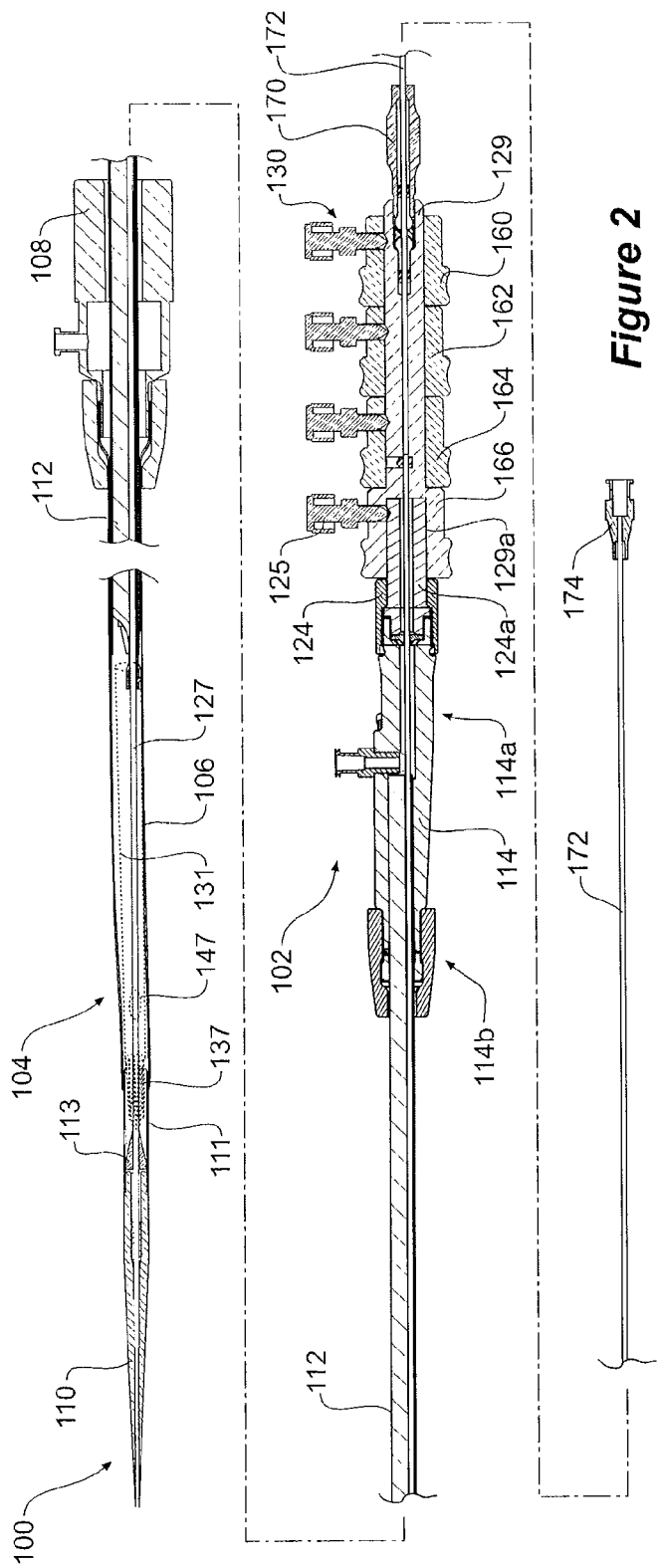
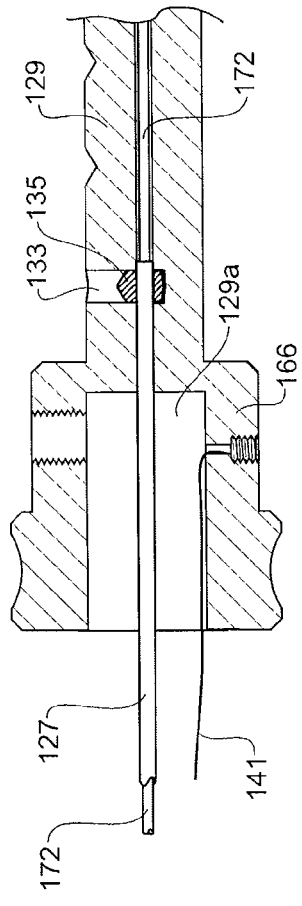
Figure 2
Figure 2A

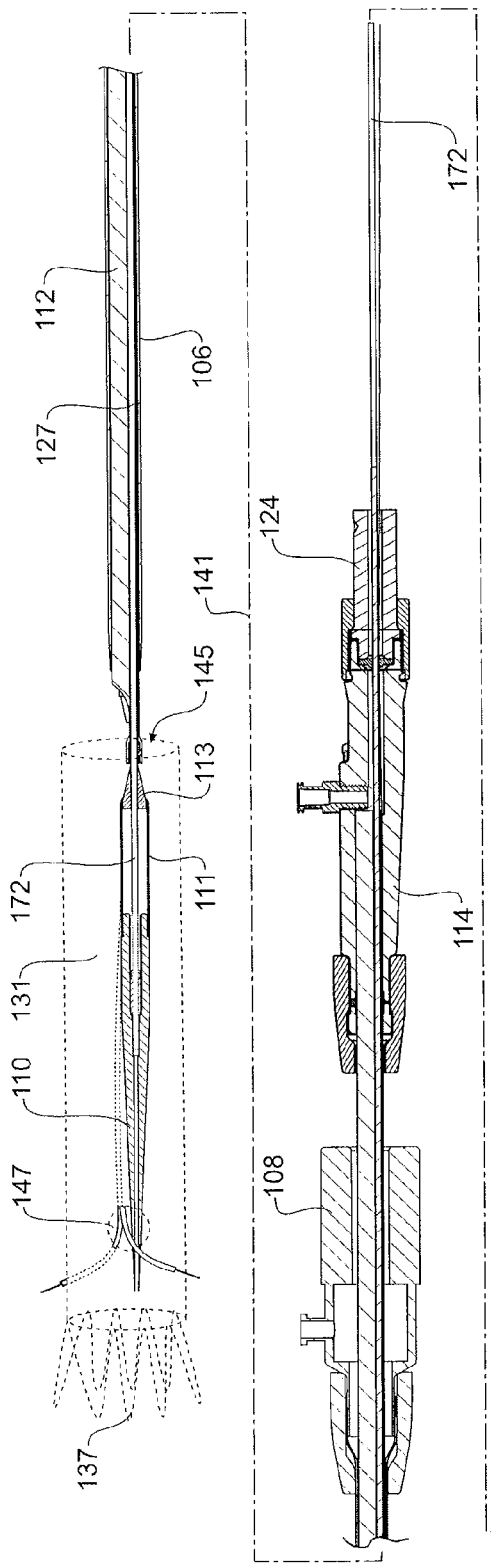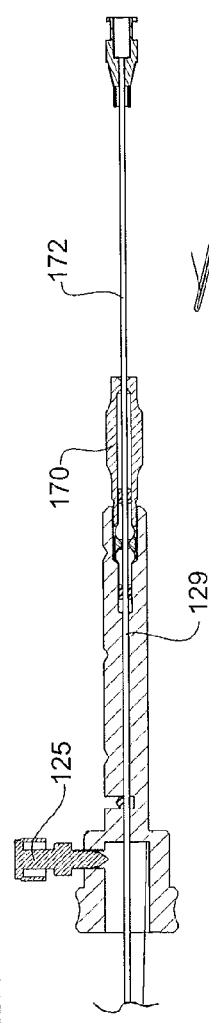
*Figure 5*
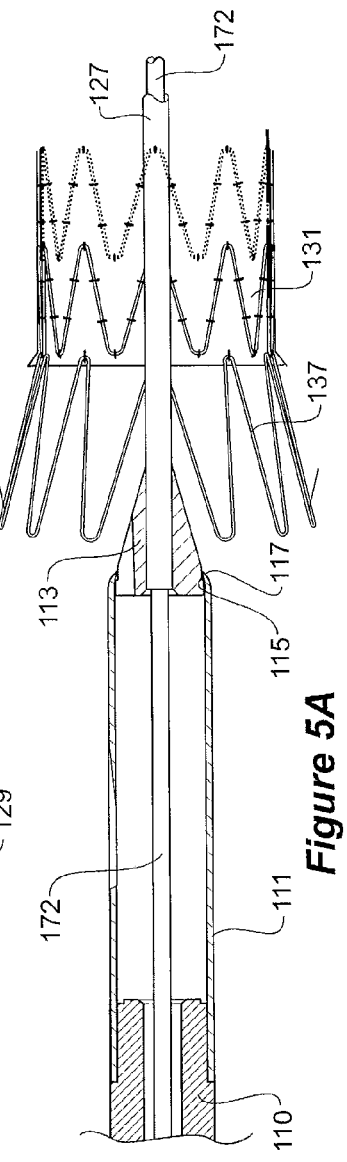
*Figure 5A*

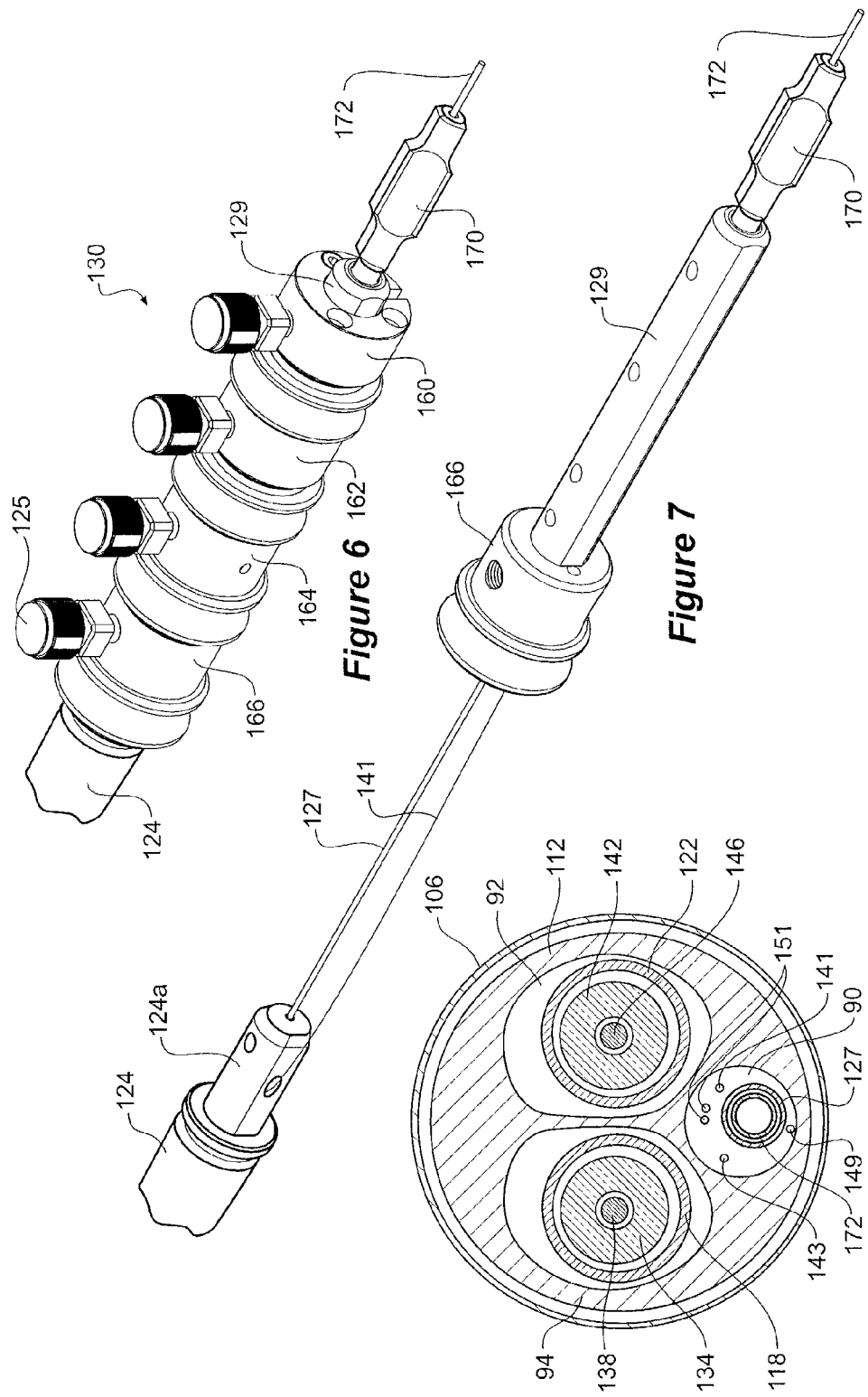

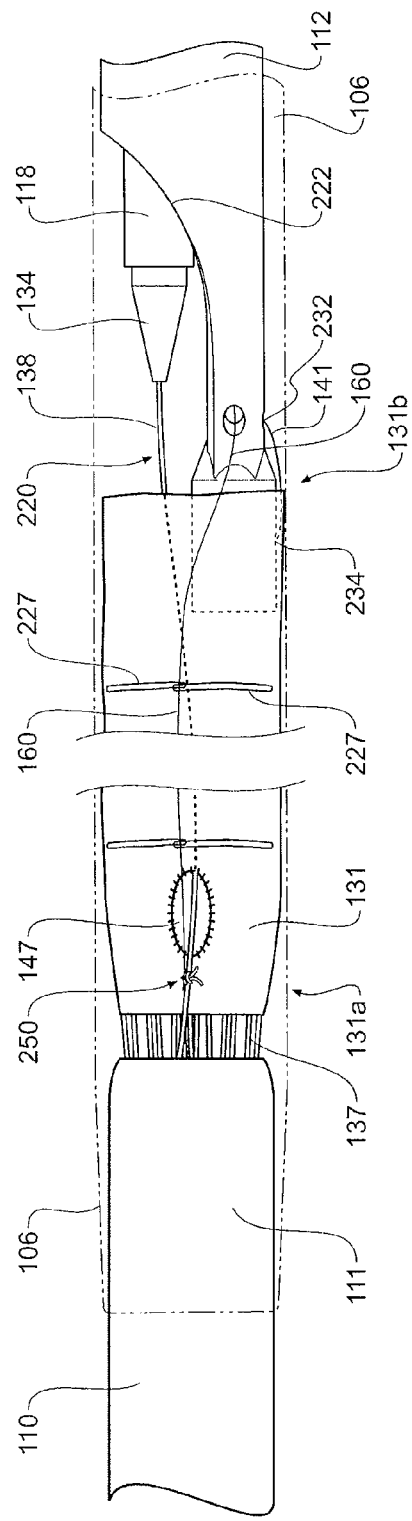
*Figure 12*
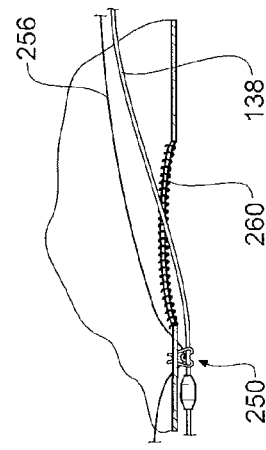
*Figure 15*
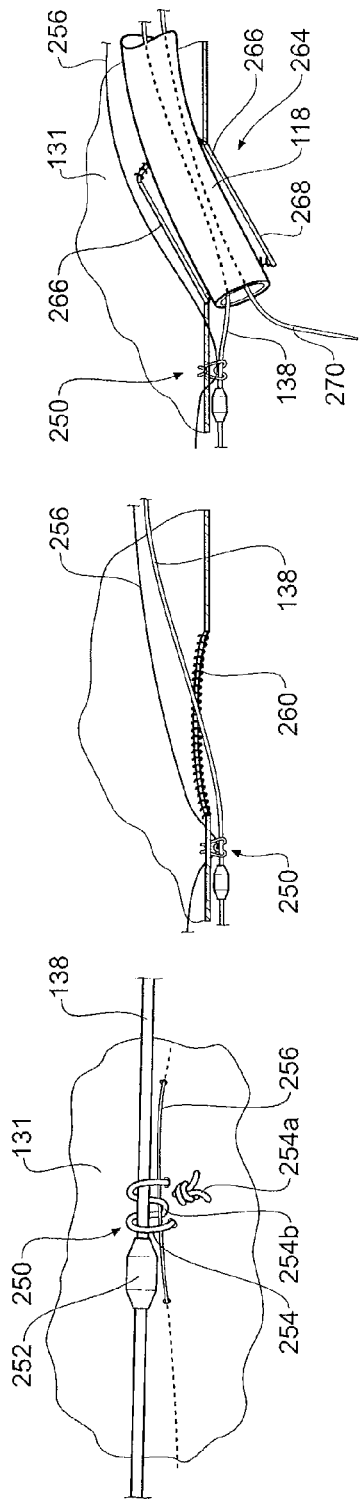
*Figure 14*
*Figure 13*

PRE-LOADED MULTIPORT DELIVERY DEVICE

RELATED APPLICATIONS

The present patent document is a continuation of application Ser. No. 13/153,753, filed Jun. 6, 2011, which claims the benefit of priority to Australian Patent Application No. 2010202487, filed Jun. 15, 2010, and entitled "Pre-Loaded Multiport Delivery Device," the entire contents of each of which are incorporated herein by reference.

TECHNICAL FIELD

This invention relates to a medical device and more particularly to a device for introduction or delivery of a stent graft into the vasculature of a patient.

SPECIFICATIONS REFERRED TO HEREIN

U.S. Pat. No. 7,435,253 entitled "Prosthesis and a Method of Deploying a Prosthesis"

U.S. patent application Ser. No. 11/507,115, filed Aug. 18, 2006 entitled "Assembly of Stent Grafts"

PCT/US09/03393 (Published WO 2009/148602 Dec. 10, 2009) entitled "Top Cap Retrieval Arrangement"

U.S. patent application Ser. No. 11/904,834, filed Sep. 28, 2007 entitled "Endovascular Delivery Device"

U.S. patent application Ser. No. 11/507,115, filed Aug. 18, 2006 entitled "Assembly of Stent Grafts"

U.S. patent application Ser. No. 10/962,765, filed Oct. 12, 2004 entitled "Fenestrated Stent Grafts"

U.S. patent application Ser. No. 11/706,114, filed Feb. 13, 2007 entitled "Side Branch Stent Graft Construction"

BACKGROUND OF THE INVENTION

It is known to introduce endovascular stent grafts into the vasculature of a patient to bridge an aneurism or damaged portion of the wall of the vasculature. Problems can occur, however, where the damage to the vasculature includes or is adjacent to a branch vessel from a main artery because occlusion of the branch vessel may cause permanent damage to the patient.

Examples of such branch vessels are the renal and the mesenteric arteries extending from the aorta.

Fenestrations in a stent graft have been proposed to allow access to the branch vessel from a main stent graft but it is often necessary to provide a side branch graft to maintain access into the branch vessel. Catheterisation of such a branch vessel from a delivery device through the fenestration enables deployment of a covered stent or uncovered stent into the side vessel. This invention provides an improved apparatus for catheterisation and deployment of side branch grafts.

Throughout this specification the term distal with respect to a portion of the aorta, a delivery device or a prosthesis means the end of the aorta, delivery device or prosthesis further away in the direction of blood flow away from the heart and the term proximal means the portion of the aorta, delivery device or end of the prosthesis nearer to the heart. When applied to other vessels similar terms such as caudal and cranial should be understood.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention. 2.

SUMMARY OF THE INVENTION

In one form the invention comprises a pre-loaded stent graft delivery device in combination with a stent graft, the stent graft delivery device comprising;

a guide wire catheter having a guide wire lumen therethrough;

a handle assembly at a distal end of the guide wire catheter, the handle including a multiport manifold; a nose cone dilator at the proximal end of the guide wire catheter, the nose cone dilator comprising a distal end and a distally facing capsule on the distal end of the nose cone dilator; a pusher catheter extending from the manifold towards the a nose cone dilator, the pusher catheter comprising a longitudinal pusher lumen therethrough and the guide wire catheter extending through the pusher lumen and the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region; the pusher catheter comprising at least one longitudinal auxiliary lumen extending from the manifold to the proximal end of the pusher catheter; a sheath hub on the pusher catheter and a sheath arrangement extending from the sheath hub to the nose cone dilator, the sheath arrangement being coaxial with and surrounding the guide wire catheter; the stent graft comprising a tubular body of a biocompatible graft material, the tubular body comprising a peripheral wall and defining a lumen therethrough, a proximal end, a distal end, at least one fenestration in the peripheral wall and a proximally extending exposed self expanding stent; the stent graft being received on the guide wire catheter in the stent graft retention region and within the sheath, the proximally extending exposed self expanding stent of the stent graft being releasably retained in the distally facing capsule on the distal end of the nose cone dilator; an indwelling access sheath within the or each auxiliary lumen, the indwelling access sheath extending through the manifold from external thereof and having a proximal end terminating distally of the stent graft; an indwelling guide wire within the or each access sheath;

the indwelling guide wire extending proximally of the access sheath through the stent graft and exiting the at least one fenestration and extending proximally to the distally facing capsule;

whereby upon deployment of the stent graft into the vasculature of a patient the indwelling guide wire can be used to facilitate cathertisation of a side branch or target vessel or be used to stabilise the access sheath during catheterisation, advancement of the access sheath into the target vessel and deployment of a covered or uncovered stent therein through the access sheath.

Preferably a dilator extends through the or each access sheath and comprises a dilator tip at the proximal end of the or each access sheaths, the dilator being able to be withdrawn through the access sheath.

Preferably the manifold comprises at least one port and a haemostatic seal assembly in the or each port and the access sheath extending through the haemostatic seal assembly. More preferably the manifold comprises two side ports and a through bore, the two side ports extending distally at an angle from the through bore, the pusher catheter comprising two auxiliary lumens and two side apertures at its distal end and the two side apertures opening respectively into the two auxiliary lumens, the pusher catheter being received into the through bore of the manifold such that the two side apertures open respectively into the two side ports thereby providing a path for the access catheters.

Preferably pusher catheter comprises two longitudinal auxiliary lumens and the proximal end of the pusher catheter comprises an attachment boss and a scalloped end to provide exit ports for the auxiliary lumens.

Preferably the handle assembly comprises a proximal handle portion and a distal handle portion, the distal handle portion being movable longitudinally with respect to the proximal handle portion, the guide wire catheter extending through each of the distal handle portion and the proximal handle portion, the guide wire catheter being releasably affixed at a distal end to the distal handle portion, the nose cone dilator and the distal handle portion being movable longitudinally with respect to the proximal handle portion whereby the nose cone dilator can be retracted independently of the manifold and pusher catheter.

Preferably the pre-loaded stent graft delivery device comprises a distal retrieval taper device in the distally facing capsule, the distal retrieval taper device being mounted onto the guide wire catheter and movable longitudinally with respect to the guide wire catheter, a distal retrieval catheter coaxially on the guide wire catheter and movable longitudinally with respect to the guide wire catheter, the distal retrieval catheter being fixed to the distal retrieval taper device at a proximal end and to the distal handle portion at a distal end, whereby movement of the guide wire catheter in a proximal direction with respect to the distal handle portion moves the distally facing capsule with respect to the distal retrieval taper device such that the distally facing capsule can move over the distal retrieval taper device to allow the distal retrieval taper device to extend from the capsule whereby to provide a smooth transition from the otherwise distal opening of the capsule to enable retraction of the nose cone dilator through a deployed stent graft.

Preferably the proximal handle portion is releasably fastened to the distal handle portion.

The stent graft can include diameter reducing ties and the delivery device further includes a release arrangement on the handle assembly for the diameter reducing ties, the release arrangement for the diameter reducing ties comprising a first release grip on the handle and a release wire extending from the first release grip to the diameter reducing ties.

There can be further included a retention arrangement for the distal end of the stent graft comprising a second release grip on the handle assembly and at least one trigger wire extending from the second release grip through the longitudinal pusher lumen and exiting the pusher lumen at the attachment boss and engaging the distal end of the stent graft.

The indwelling guide wire extending through the stent graft and exiting the at least one fenestration and extending proximally within the main sheath can comprise a releasable fastening whereby the indwelling guide wire is releasably fastened to the peripheral wall of the stent graft proximally of the fenestration to stabilise the indwelling guide wire during advancement of the dilator and access sheath and catheterisation of the branch vessel. The releasable fastening of the indwelling guide wire can comprise a release wire stitched in to peripheral wall of the stent graft proximally of the fenestration, an engagement protrusion of the indwelling guide wire and a thread engaged around the release wire and the indwelling guide wire distally of the engagement protrusion whereby upon retraction of the release wire the suture is released from engagement with the indwelling guide wire.

It will be seen that by the various embodiments of the invention there is provided a device where the pusher catheter and the sheaths for each of the side branch catheterisation devices are included within the main sheath of the stent graft with each of the components being able to be manipulated separately. During deployment and before final placement of the covered or uncovered side branch stents the nose cone dilator can be retracted to distal of the fenestrations by movement of the distal handle portion.

This then generally describes the invention but to assist with understanding reference will now be made the accompanying drawings which show preferred embodiments of the invention.

BRIEF DESCRIPTION OF THE DRAWINGS

FIG. 2 shows a longitudinal cross sectional view of the embodiment of a stent graft delivery device of FIG. 1 according the present invention;

FIG. 2A shows the embodiment shown in FIG. 1 and in particular a detail of a part of the distal handle portion;

FIG. 5 shows the embodiment shown in FIG. 41 in longitudinal cross section;

FIG. 5A shows the embodiment shown in FIG. 1 and in particular a detail of a part of the nose cone dilator and capsule with the distal retrieval taper in its distal position;

FIG. 6 shows a perspective view of part of the handle of the embodiment shown in FIG. 1;

FIG. 7 shows the view of FIG. 6 in an activated condition;

FIG. 8 shows a transverse cross sectional view of the pusher catheter portion of the embodiment shown in FIG. 1 along the line 8-8';

FIG. 12 shows a schematic detailed side view of the stent graft retained on the delivery device;

FIG. 13 shows a method of releasable retention of the indwelling guide wire,

FIGS. 14 and 15 show two embodiments of fenestrations suitable for the present invention.

DETAILED DESCRIPTION OF THE DRAWINGS

Figure 1:
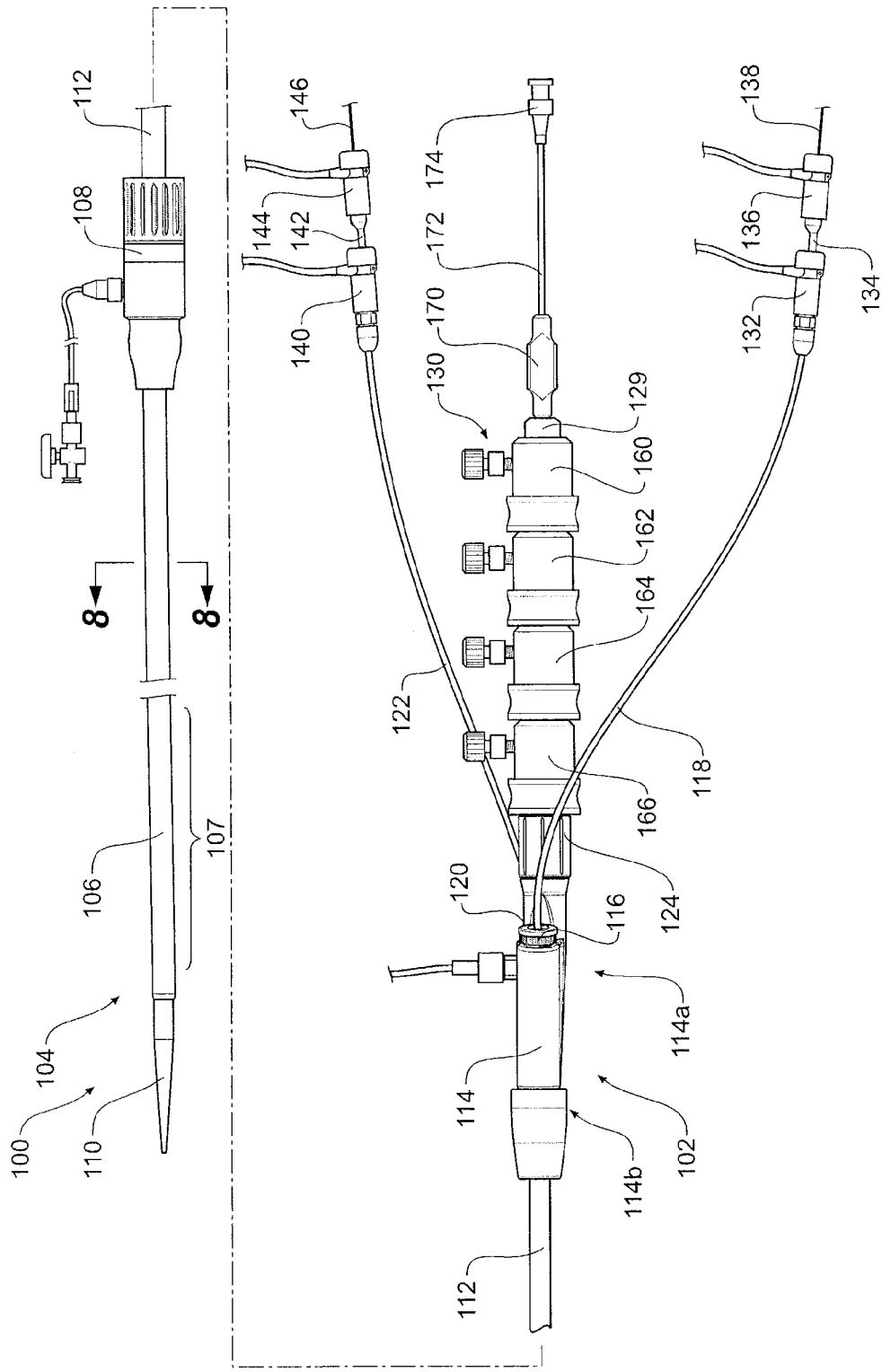
FIG. 1 shows a first embodiment of a pre-loaded stent graft delivery device according to the present invention.

The drawings, FIGS. 1 to 11D show a first embodiment of a pre-loaded delivery device according to the present invention.

The delivery device 100 comprises a handle and manifold assembly 102 and introduction portion 104 intended to be deployed into the patient by the known Seldinger method. More specifically the introduction section 104 includes a sheath 106 extending from a sheath hub 108 to a nose cone dilator 110. A stent graft 131 is retained within the outer sheath 106 in the region 107 just distal of the nose cone dilator 110.

The sheath hub and haemostatic seal 108 is positioned over a pusher catheter 112 which extends from and is connected into a manifold 114 as is discussed in more detail below. The manifold 114 has a proximal end 114b into which is affixed the pusher catheter 112 and two access ports 116, 120 at its distal end 114a. Access port 116 which has a haemostatic seal 117 is for a first access sheath 118. Access port 120 which has a haemostatic seal 121 is for a second access sheath 122. At the rear end 114a of the manifold a handle assembly 130 is connected. The handle assembly 130 includes trigger wire release mechanisms and can be separated into two parts is as discussed below.

The access sheath 118 extends to a haemostatic seal 132 through which extends a dilator 134. On the dilator 134 is a dilator haemostatic seal 136 through which extends an indwelling guide wire 138.

The access sheath 122 extends to a haemostatic seal 140 through which extends a dilator 142. On the dilator 142 is a dilator haemostatic seal 144 through which extends an indwelling guide wire 146.

The handle assembly 130 includes a proximal handle portion 124 which is affixed to the rear of the manifold 114. The handle assembly 130 also includes a distal handle portion 129. The distal handle portion 129 has a proximal recess 129a which fits over a distal extension 124a of the proximal handle portion 124 and a locking screw 125 releasably locks the two handle portions together.

The distal handle portion 129 of the handle assembly 130 includes trigger wire release mechanisms releasably mounted onto it from its distal end as follows. Trigger wire release 160 is for the release of the stabilisation retention of indwelling guide wires as will be discussed below. Trigger wire release 162 is for diameter reducing ties as will be discussed below. Trigger wire release 164 is for a retention trigger wire for the exposed stent in the capsule as will be discussed below. Trigger wire release mechanism 166 is for the distal end of the graft as will be discussed below. Trigger wire release mechanism 166 is also part of the distal portion of the handle 129 and moves with it.

U.S. patent application Ser. No. 11/507,115, filed Aug. 18, 2006 entitled "Assembly of Stent Grafts" teaches the use of diameter reducing ties for stent grafts and the teachings therein are incorporated herein in their entirety.

A pin vice 170 is at the rear of the handle assembly 130 and the guide wire catheter 172 for the delivery device extends through the pin vice 170 and is locked and can be released for movement with respect to the distal portion of the handle 130 by the pin vice. The guide wire catheter 172 terminates in a syringe point 174 to enable flushing liquid and radiopaque medium to be deployed through the delivery device.

The introduction portion 104 of the stent graft delivery device 100 has the nose cone dilator 110 and at the distal end of the nose cone dilator 110 is a distally opening capsule 111 for the receipt of an exposed stent 137 of a stent graft 131. The capsule 111 has a slightly in-turned distal end 117 (see FIGS. 4A and 5A). This has two purposes, a first is to assist with engagement of the sheath 106 of the delivery device when the nose cone dilator 110 is retracted into the sheath 106 and a second is to prevent complete withdrawal of a distal retrieval taper device 113 from the capsule as will be discussed below. The guide wire catheter 172 passes through and is fastened to the nose cone dilator 110 at its proximal end and passes through the handle assembly 130 of the delivery device. The pin vice arrangement 170 at the distal end of the distal handle portion 129 locks movement of the guide wire catheter 172 with respect to the distal portion of the handle 129 and can be loosened to allow relative motion between these components as discussed below.

Figure 2B:
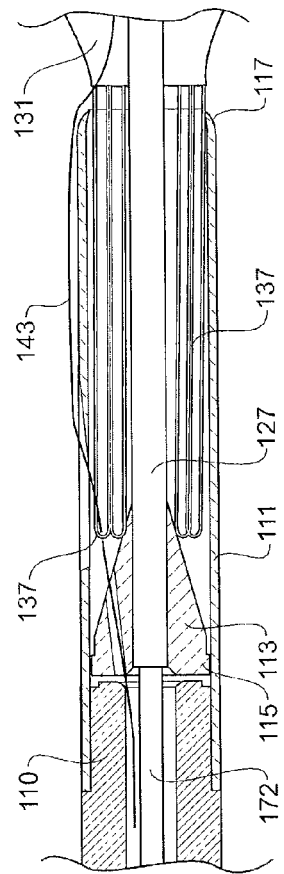
FIG. 2B shows the embodiment shown in FIG. 1 and in particular a detail of a part of the nose cone dilator and capsule with the distal retrieval taper.

The stent graft 131 shown in FIG. 2 for instance comprises a tubular body of a biocompatible graft material such as Dacron, expanded PTFE or Thoralon, a polyurethane material. The stent graft is supported by self expanding stents (not shown for clarity). A proximally extending exposed stent 137 assists with providing infra-renal fixation of the deployed stent graft. The stent graft has two fenestrations 147 which are provided to give access to the renal arteries. The stent graft is retained on the delivery device by proximal retention of the exposed stent 137 into the capsule 111 of the delivery device and distally by a trigger wire retention 145 as will be discussed in detail below. Diameter reducing ties can be used to hold the stent graft in a diameter reduced condition during the initial catheterisation of a side branch because it may still be necessary to move the stent graft proximally or distally or rotate it. In the diameter reduced condition this is still possible whereas when released to full diameter this may not be possible.

U.S. Pat. No. 7,435,253 entitled "Prosthesis and a Method of Deploying a Prosthesis" teaches arrangements for retaining a stent graft or prosthesis on a delivery or deployment device and allowing for independent rotational and translational movement of each end of the stent graft and the teachings therein are incorporated herein in their entirety.

As can be seen particularly in FIGS. 5 and 5A the distal retrieval taper device 113 fits coaxially around the guide wire catheter 172 and can move longitudinally along the guide wire catheter. A retrieval catheter 127 is mounted coaxially around the guide wire catheter 172 and can move longitudinally along the guide wire catheter. At its proximal end the retrieval catheter 127 is joined to the distal retrieval taper device 113 and at its distal end the retrieval catheter 127 is joined to the distal handle portion 129 at 133 by a suitable adhesive 135. For this purpose apertures are provided into the handle and adhesive is applied through these apertures. FIG. 2A shows detail of the mounting of the retrieval catheter into the distal handle portion.

The distal retrieval taper device is shown in detail in FIGS. 5 and 5A. The distal retrieval taper device 113 has an enlarged shoulder 115 at its proximal end. The shoulder is sized so that it is of greater diameter than the smallest part of the in-turned distal end 117 of the capsule 111. By this arrangement the distal retrieval taper device can move through the capsule but cannot be fully removed from the capsule. The retrieval catheter 127 is coaxial with the guide wire catheter 172. At its proximal end the retrieval catheter 127 is affixed to the distal retrieval taper device and at its distal end the retrieval catheter 127 is affixed to the distal handle portion 129 as shown in FIG. 2A. This means that movement of the guide wire catheter 172 proximally with respect to the distal handle portion 129, after release of the pin vice 170 will move the nose cone dilator 110 and capsule 111 with respect to the distal retrieval taper device with the effect that the distal retrieval taper extends from the capsule thereby providing a smooth tapered surface for retrieval of the nose cone dilator through the stent graft. Locking of the pin vice after the distal retrieval taper 113 has been moved to the distal end of the capsule 111 ensures that all of the distal retrieval taper, the capsule, the nose cone dilator and the distal handle portion all move together.

U.S. Provisional Patent Application Ser. No. 61/130,952, filed Jun. 4, 2008 and entitled "Top Cap Retrieval Arrangement" teaches distal retrieval taper devices (referred to therein as tapered plugs) and the teaching therein is incorporated herein in its entirety.

By this arrangement the nose cone dilator can be moved to a distal position with respect to fenestrations in the stent graft so that the nose cone dilator and distally opening capsule does not interfere with the deployment of side branch covered or uncovered stent grafts through such fenestrations nor does any subsequent retraction of the nose cone dilator interfere with the deployed of side branch side branch covered or uncovered stent grafts.

U.S. patent application Ser. No. 11/904,834, filed Sep. 28, 2007 entitled "Endovascular Delivery Device" teaches apparatus and methods of deployment of stent grafts and side branch stent graft into fenestration of such stent grafts and the teaching therein is incorporated herein in its entirety. The use of the stabilisation retention of the indwelling guide wire is particularly discussed therein.

As can be seen particularly in FIG. 8, which is a transverse cross section along the line 8-8' as shown in FIG. 1, the pusher catheter 112 is surrounded by the sheath 106. The pusher catheter has three longitudinally extending lumens. A first lumen is the guide wire lumen 90 and this lumen is off-set from the centre of the pusher catheter to allow for two auxiliary lumens 92 and 94. The guide wire lumen 90 has passing through it the guide wire catheter 172 and coaxially around that the retrieval catheter 127. Also in the guide wire lumen are the trigger wires for the diameter reducing ties 149, the top capsule 143, the distal retention 141 and the auxiliary guide wire stabilisation 151. The auxiliary lumen 94 has the access sheath 118 extending through it and the dilator 134 and guide wire 138 extend through the access sheath 118. The auxiliary lumen 92 has the access sheath 122 extending through it and the dilator 142 and guide wire 146 extend through the access sheath 122.

Figure 9:
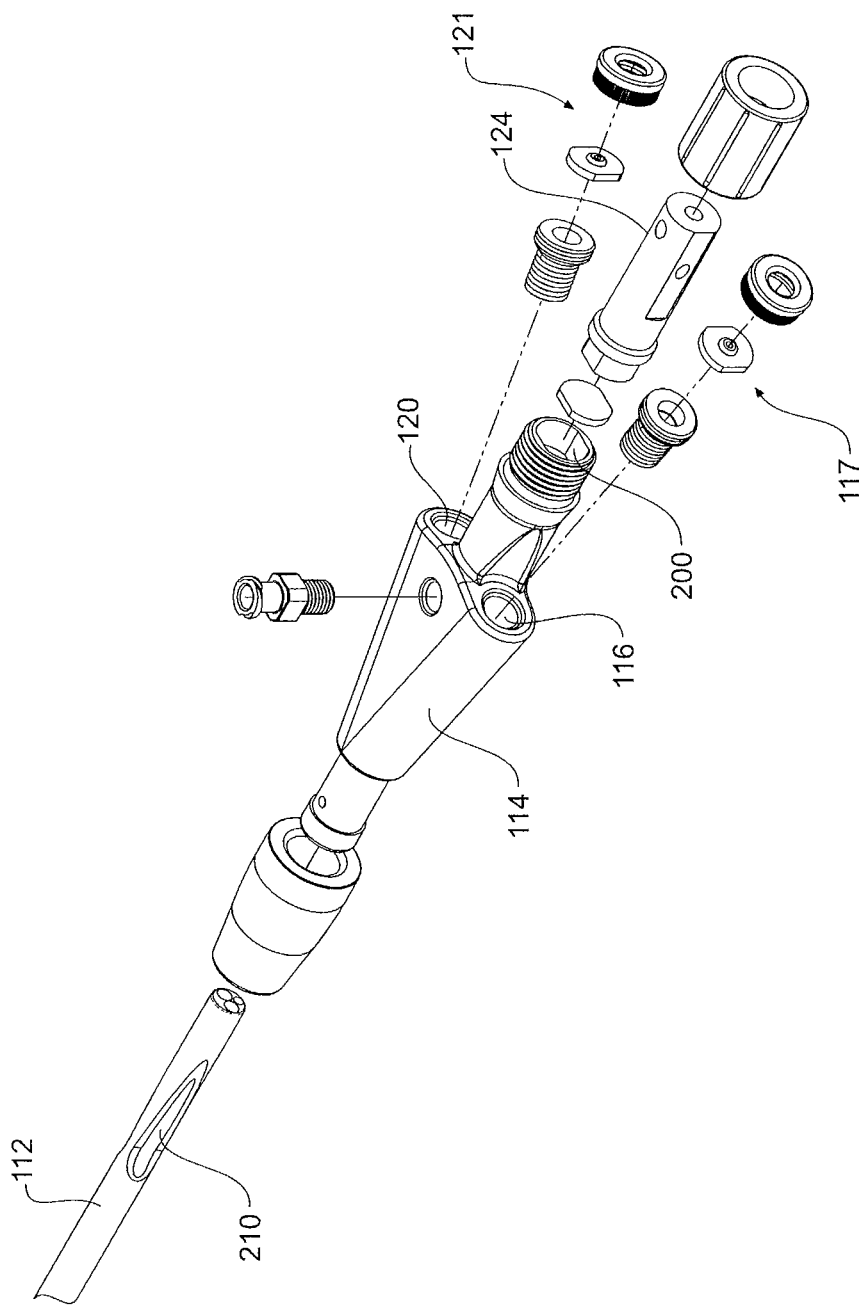
FIG. 9 shows an exploded view of a manifold of an embodiment of the present invention.
Figure 10A:
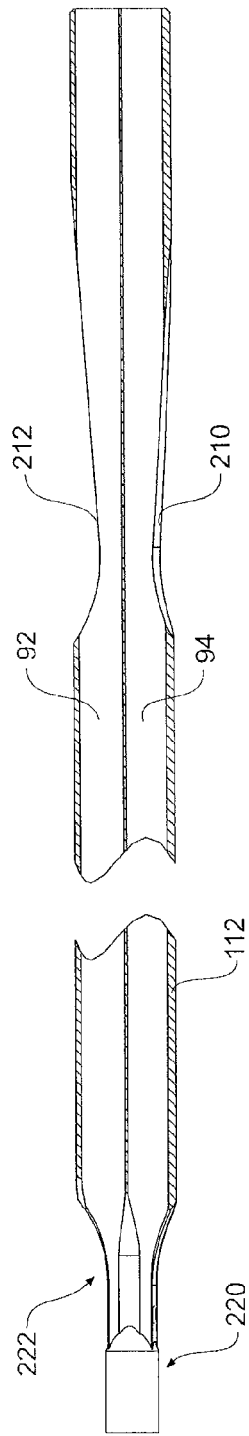
FIGS. 10A to 10D show various views of the pusher catheter of an embodiment of the present invention.
Figure 10B:
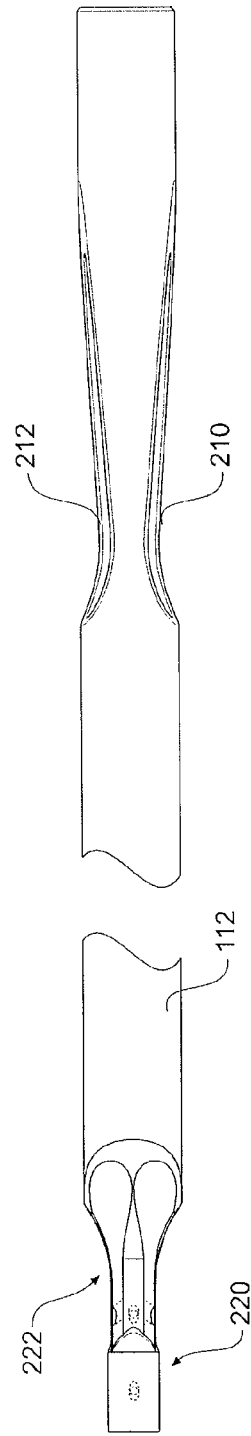
Figure 10C:
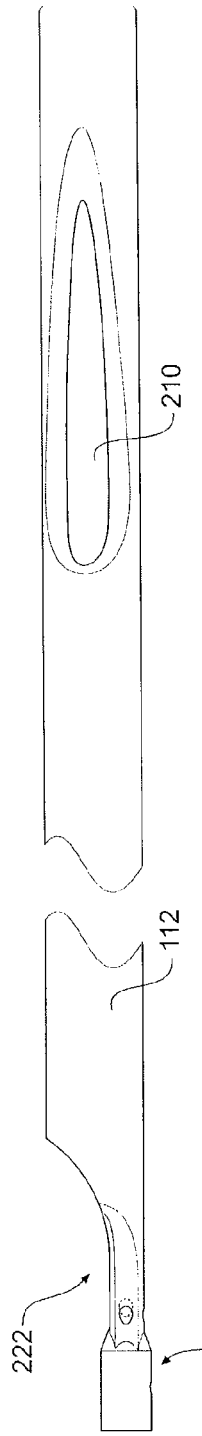
Figure 10D:
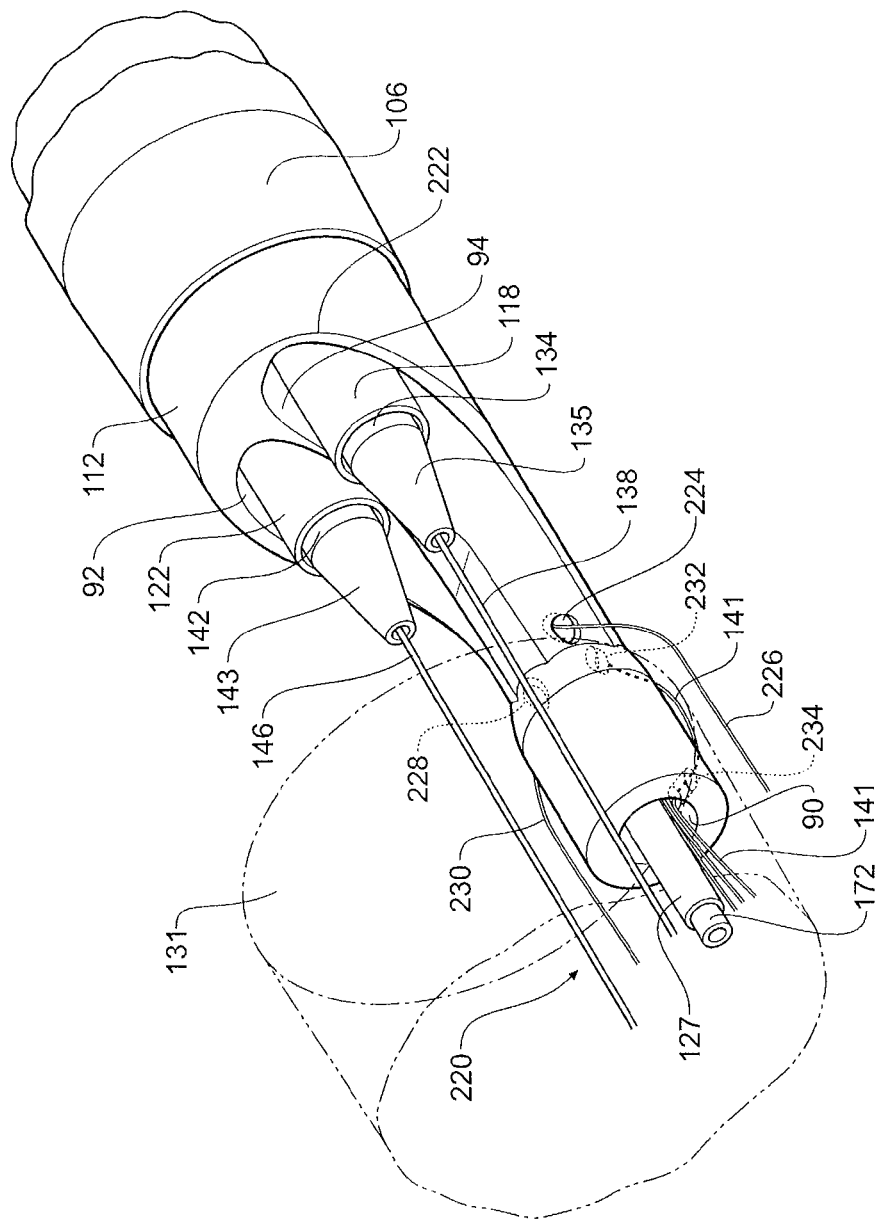
Figure 11:
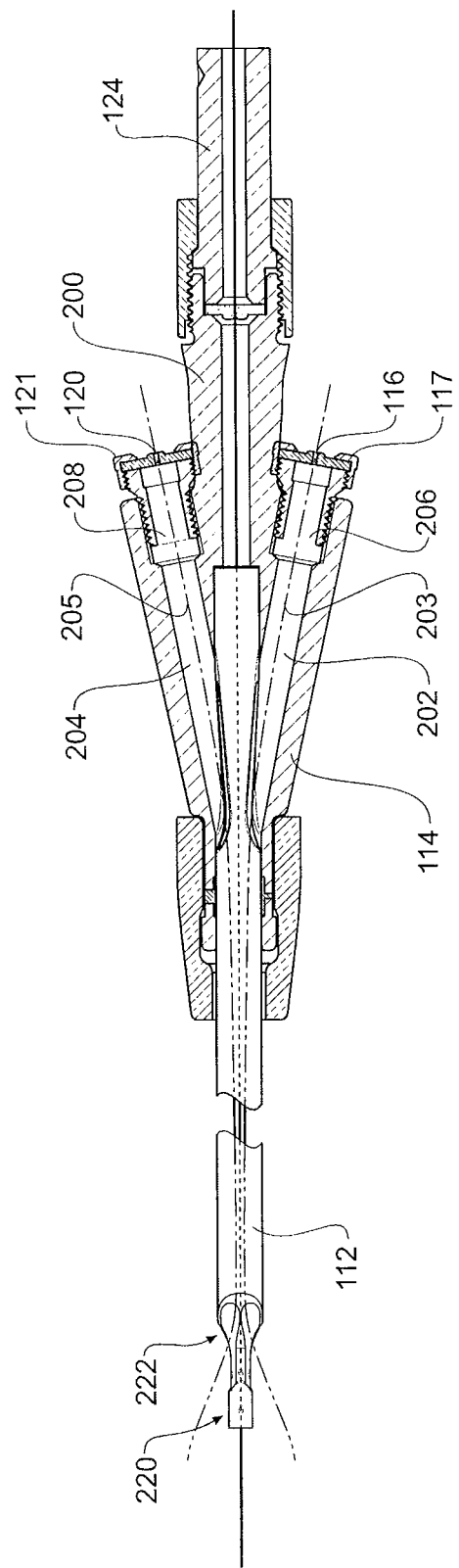
FIG. 11 shows a cross sectional view of the assembly of a manifold and pusher catheter according to the present invention.

The manifold 114 and pusher catheter is shown in more detail in FIGS. 9 to 11.

The manifold 114 has a through bore 200 and angled side ports 202 and 204. The pusher catheter has three lumens as shown on FIG. 8, the guide wire lumen 90 and this lumen is off-set from the centre of the pusher catheter to allow for two auxiliary lumens 94 and 92. As can be seen in FIGS. 10A to 10C the pusher catheter 112 has two side apertures 210 and 212 which open from the side of the pusher catheter into the respective lumens 92 and 94. These side apertures are elongate and tapered towards the distal end. When the pusher catheter is pushed into the through bore 200 of the manifold 114 the side apertures in the pusher catheter align with the respective angled side ports 202 and 204 thereby providing an uninterrupted lumen from the access port 116 for the first access sheath 118 into the pusher lumen 94 along the dotted line 203 and from access port 120 for a second access sheath 122 into the pusher lumen 92 along the dotted line 205.

As can be best seen in FIG. 10A to 10D, at the proximal end of the pusher catheter is an attachment boss 220 and a scalloped end 222 to provide exit ports for the two auxiliary lumens 92 and 94. The guide wire lumen 90 opens out at the proximal end of the attachment boss 220 and to each side of the attachment boss there are apertures for trigger wires. Aperture 224 is for trigger wire 226 which is used for the diameter reducing ties on one side of the stent graft 131. A corresponding aperture 228 and the other side of the attachment boss 220 is for the trigger wire 230 for the other side of the stent graft 131.

Trigger wire 141 extends out of aperture 232 in the attachment boss 220 and engages into the stent graft 131 before re-entering the attachment boss at aperture 234 and exiting the guide wire lumen 90 at the proximal end of the pusher catheter 112.

Extending out of the two auxiliary lumens 92 and 94 are the auxiliary catheters 122 and 118 respectively. From the proximal ends of the respective auxiliary catheters 118 and 122 extend dilators 134 and 142. The auxiliary guide wires 138 and 146 extend through the dilators.

FIG. 12 shows detail of the stent graft 131 and its retention system in the region 107 as shown in FIG. 1. In particular there is detail shown of the distal attachment, the diameter reducing ties and the proximal retention.

The stent graft 131 is retained within the sheath 106 and concentrically around the guide wire catheter 172 and retrieval catheter 127. The stent graft has a fenestration 147 towards its proximal end. In use the stent graft is deployed so that the fenestration is substantially aligned with a renal artery and it is intended to catheterise the renal artery through the fenestration to deploy a covered or uncovered side branch stent or stent graft into the renal artery. The stent graft has a proximally extending exposed stent 137 at is proximal end 131a. In its ready to deploy condition the proximally extending exposed stent 137 is received into the capsule 111 at the distal end of the nose cone dilator 110. At its distal end 131b the stent graft is retained to the attachment boss 220 at the proximal end of the pusher catheter 112. Trigger wire 141 engages the distal end of the stent graft. Trigger wire 141 extends out of aperture 232 in the attachment boss 220 and engages into the stent graft 131 before re-entering the attachment boss through aperture 234 into the guide wire lumen 90 and exiting the guide wire lumen 90 at the proximal end of the pusher catheter 112. At its distal end the trigger wire 141 is attached to the trigger wire release mechanism 166. Trigger wire release mechanism 166 is also part of the distal portion of the handle 129.

The stent graft 131 has diameter reducing tie arrangements to retain it in a partially diameter reduced condition even after the sheath 106 has been retracted during deployment. The diameter reducing tie arrangement are on each side of the stent graft and comprise a trigger wire 160 stitched along the graft material on either side of the stent graft and loops of filament such as suture thread 227 engaged around the trigger wire and a portion of the graft material part way around the stent graft and then drawn tight.

U.S. patent application Ser. No. 11/507,115, filed Aug. 18, 2006 entitled "Assembly of Stent Grafts" teaches apparatus and methods of diameter reduction of stent grafts and the teaching therein is incorporated herein in its entirety.

FIG. 13 shows detail of the retention system 250 by which the guide wires 138 (for instance) is stabilised proximally of the fenestration 147 (for instance). The guide wire 138 has a protrusion 252 which can be fastened with respect to the guide wire by solder, crimping, welding or gluing. A suture thread 254 is looped 254b around the guide wire 138 distally of the protrusion 252 and around a release wire 256 which is stitched through the material of the stent graft 131 and then the suture thread 254 is sewn at 254a into the material of the stent graft 131. When the release wire 256 is retracted the loop 254b of the suture thread 254 is released and the guide wire 138 can be retracted. In the meantime the retention system stabilises the guide wire.

FIG. 14 shows a cross section of a simple fenestration in cross section with the stabilised auxiliary guide wire extending through it. In this embodiment the fenestration 260 is reinforced with a ring of resilient wire such as nitinol wire. The auxiliary guide wire 138 passes through the fenestration and is restrained just proximal of the fenestration using a retention system 250 as shown in FIG. 13.

U.S. patent application Ser. No. 10/962,765, filed Oct. 12, 2004 entitled "Fenestrated Stent Grafts" teaches fenestrations in stent grafts and the teaching therein is incorporated herein in its entirety.

FIG. 15 shows a cross section of an alternative fenestration arrangement incorporating a low profile side arm with the stabilised auxiliary guide wire extending through it. In this embodiment the fenestration 264 is in the form of a low profile side arm 264. The low profile side arm 264 has an inner portion 266 which extends within the tubular body of the stent graft and an outer portion 268 which extends outside of the tubular body of the stent graft and is stitched into the periphery of the fenestration. The stitching extends circumferentially and diagonally from one end of the low profile side arm to the other.

In FIG. 15 the fenestration is shown at the stage of deployment at which the first access sheath 118 has been advanced over the auxiliary guide wire 138 until it just extends out of the low profile side arm 264. The auxiliary guide wire 138 passes through the fenestration and is restrained just proximal of the fenestration using a retention system 250 as shown in FIG. 13 and this stabilises the access sheath 118 while catheterisation of a side branch artery is occurring. The dilator has been retracted and another guide wire 270 has been deployed through the access sheath 118 and this guide wire be used to catheterise of the side branch artery.

U.S. patent application Ser. No. 11/706,114, filed Feb. 13, 2007 entitled "Side Branch Stent Graft Construction" teaches low profile side arm fenestrations in stent grafts and the teaching therein is incorporated herein in its entirety.

Figure 16:
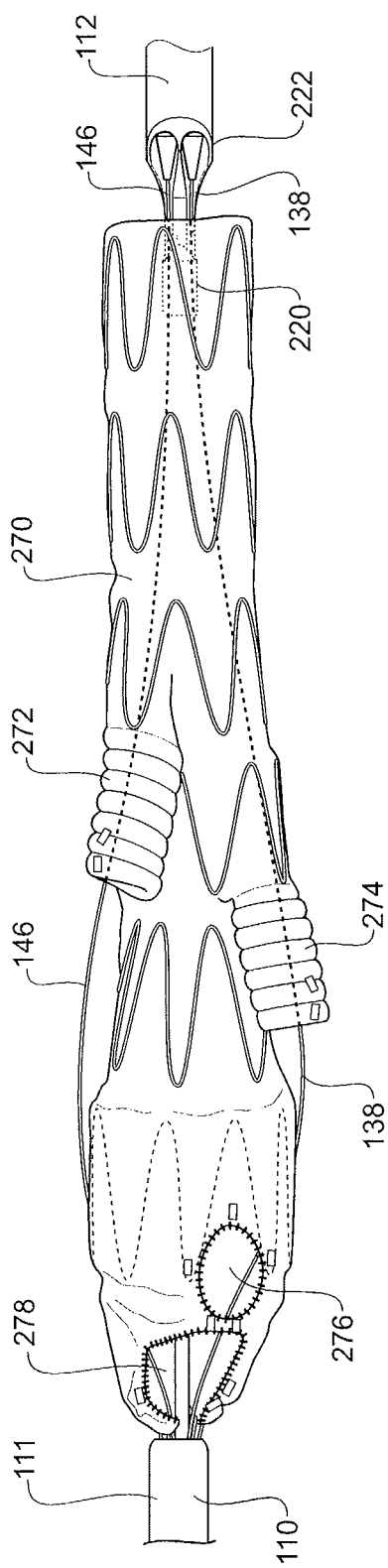
FIG. 16 shows an alternative embodiment of stent graft on a delivery device of the present invention.

FIG. 16 shows an alternative embodiment of stent graft on a delivery device of the present invention. In this embodiment the stent graft 270 has two high flexibility side arms 272 and 274 which are intended for connection to respective renal arteries, a fenestration 276 for the celiac artery and a scalloped proximal end 278 for the superior mesenteric artery. The auxiliary guide wires 138 and 146 extend from the pusher catheter 112 within the stent graft 270 and pass out through the respective two high flexibility side arms 274 and 272 and are then stitched into the graft material to extend into capsule 111 on the nose cone dilator 110. The stitching into the stent graft material proximally of the open ends of the two high flexibility side arms 272 and 274 assists in stabilisation of the side arms during the catheterisation of the renal arteries.

In the embodiment of the delivery device shown in FIGS. 1 to 14 the following components are present:

1/ Guide wire catheter 172 extending from a handle 130 to a nose cone dilator 110.
2/ Handle 130 comprising a proximal handle portion 124 and a distal handle portion 129. The handle has:
   a) Trigger wire release for top cap 164,
   b) Trigger wire release for diameter reducing ties 162
   c) Trigger wire release for stabilisation retention of indwelling guide wire 160 on the distal portion of handle with respective trigger wires.
   d) Trigger wire release for distal end of the stent graft on distal handle portion with respective trigger wire 141.
5/ Pusher catheter 112 with lumens for access sheath 92, 94 and guide wire catheter 90 joined to proximal handle portion 124 via manifold 114.
6/ Sheath 106 with sheath hub 108 on pusher catheter 112.
7/ Nose cone dilator 110 with a distally opening top capsule 111.
8/ Indwelling guide wires 138, 146 through fenestrations 147 in stent graft 131 and into top capsule 111. Indwelling guide wires go through access sheaths 118, 122.
9/ Stabilisation retention system 250 of indwelling guide wires 138 and 146 proximally of fenestration 147.
10/ Distal retrieval taper 113 in top capsule 111 coaxial with guide wire catheter 172 and a retrieval catheter 127 extending from retrieval taper 113 to and fixed to distal portion of handle 129.
11/ Access sheaths 118 and 122 having dilators 134 and 142 respectively within them and the dilators having dilator tips 135 and 143;
12/ Stent graft 131 with:
   e) Proximally extending exposed stent 137 received in top capsule 111 and a top cap trigger wire 143 retention
   f) Distal retention at 145
   g) Fenestrations for renal arteries, for instance 147
   h) Radiopaque markers (not shown)
   i) Diameter reducing ties 227 and trigger wire 160.

Introduction steps are as follows:

(a) Position the introduction part 104 of the delivery device 100 into the aorta correctly taking into account N-S position as well as rotational position with respect to target vessels and fenestrations on the stent graft 131 using markers on stent graft body. At this stage the delivery device is as shown in FIGS. 1 and 2.

(b) Withdraw the outer sheath 106 of the delivery device while continuing to check position until the distal end of the stent graft opens. At this stage the distal end of the stent graft is still retained by distal fixation, the proximal end is retained by the exposed stent retained in top capsule of the delivery device and the expansion of the stent graft is restricted by the diameter reducing ties. This stage is shown in part in FIG. 3A.

(c) Advance the access sheaths 118, 122 (left and right) on their respective indwelling guide wires 138 146 through the lumen of stent graft 131 to or through the fenestration 147 (at this stage the top capsule still retains the exposed stent and the indwelling guide wires).

(d) Position the first access sheath at the opening of the fenestration.

(e) Remove the dilator 134 of the first access sheath.

(f) Advance an additional catheter and additional guide wire (4-5 Fr) through the first access sheath and into the target vessel (e.g. renal artery). The additional catheter may have a crooked or hockey stick tip to facilitate access.

(g) Remove the guide wire from the additional catheter and re-insert a stiffer wire into the target vessel.

(h) Release the stabilisation retention system 250 of indwelling guide wires 138 via the trigger wire release 160.

(i) Retrieve the indwelling wire guide from the top cap and pull it out completely.

(j) Remove the additional catheter and replace the access sheath dilator and dilator catheter over the stiffer wire in the target vessel and advance the access sheath over the stiffer wire into the target vessel. Withdraw the access sheath dilator.

(k) Repeat steps (d) to (j) for the other of the target vessels.

(l) Advance covered stents through each of the access sheaths into the target vessels but do not release.

(m) Release the diameter reducing ties by releasing and withdrawing trigger wire release 162.

Figure 3:
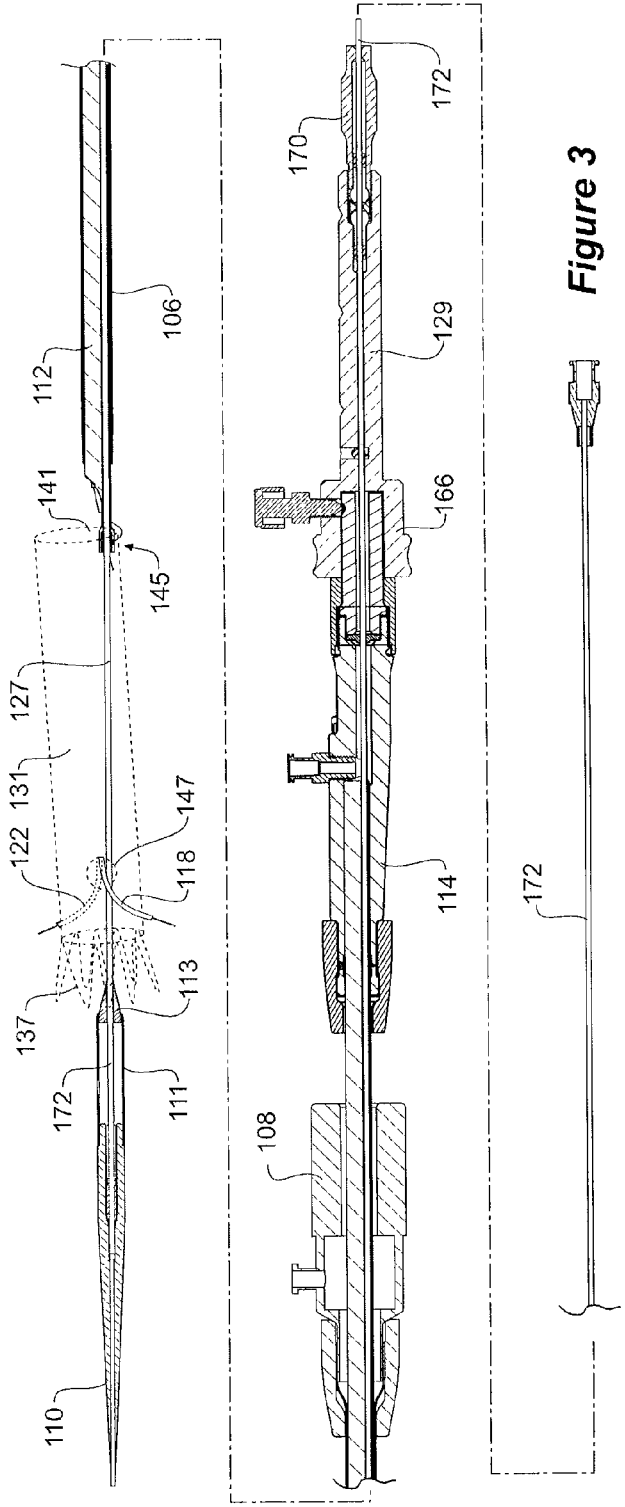
FIG. 3 shows the embodiment shown in FIG. 1 in a first partially activated condition.

(n) Release the top capsule 111 by removing the locking trigger wire 143 via trigger wire release 164, releasing the pin vice 170 and advancing the top capsule on the guide wire catheter and release the top exposed stent. At the same time the distally facing capsule moves proximally over the distal retrieval taper device to allow the distal retrieval taper device to extend from the distal end of the capsule. This stage is shown in FIG. 3.

(o) Tighten the pin vice 170.

Figure 4:
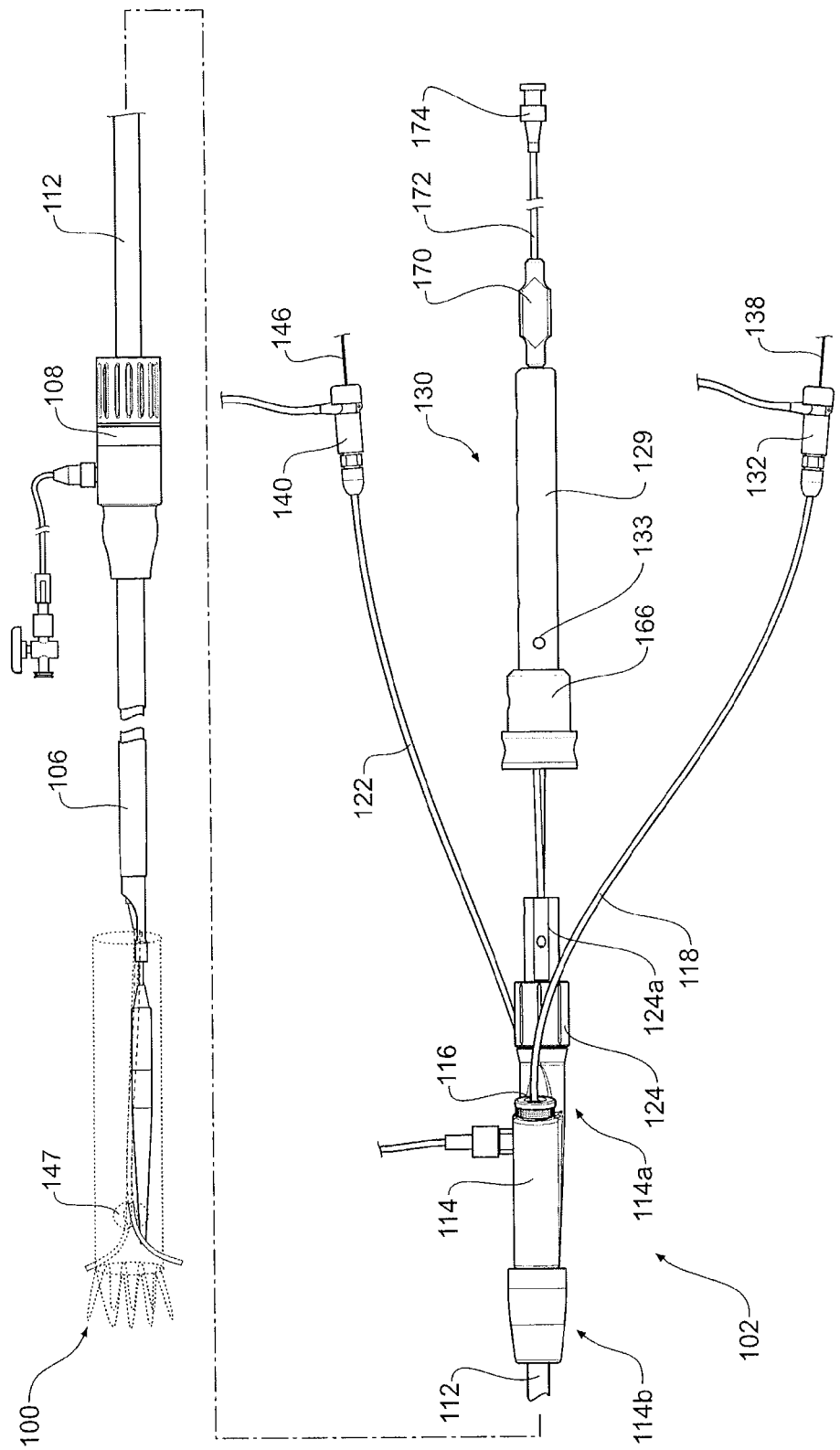
FIG. 4 shows the embodiment shown in FIG. 1 in a further partially activated condition.

(p) Retract the nose cone dilator, top cap and distal retrieval taper past the fenestration by removing the locking screw 125 of the distal handle portion and retracting distal portion of handle. This also releases the distal attachment via trigger wire 141 connected to trigger wire release 166. This stage is shown in FIGS. 4, 5 and 7.

(q) One at a time, withdraw the access sheaths from the target vessels and deploy covered stents between the fenestrations and target vessels and balloon expand if necessary including flaring within the main stent graft.

(r) Remove both access sheaths and also the guide wires from the target vessels and withdraw them from the system.

(s) Retract the nose cone dilator, top cap and distal retrieval taper to the sheath 106.

(t) Withdraw the entire assembly or leave the outer sheath in place for further deployments. Further deployment may include a bifurcated distal component.

It is seen that by this invention an arrangement is provided that by which access sheaths may extend through the introduction device and are able to be separately manipulated to enable access to renal or other arteries within the vasculature of a patient.

The invention claimed is:

1. A stent graft delivery device having two indwelling access sheaths preloaded with a stent graft on the delivery device, the stent graft delivery device comprising;
    a guide wire catheter having lumen therethrough;
    a handle assembly at a distal end of the guide wire catheter, the handle including a multiport manifold;
    a nose cone dilator at the proximal end of the guide wire catheter;
    a pusher catheter extending from the manifold towards the nose cone dilator, the pusher catheter comprising a longitudinal pusher lumen therethrough that is offset from the center of the pusher catheter and two longitudinal auxiliary lumens, the pusher catheter completely enclosing the two longitudinal auxiliary lumens radially, a sheath disposed coaxially over the pusher catheter and the stent graft, the guide wire catheter extending through the pusher lumen and the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region;
    the stent graft comprising a stent structure, graft material having a side wall, at least two fenestrations in the side wall of graft material, a proximal end, a distal end and a lumen therethrough;
    the manifold comprising two elongate side ports and a through bore, the two elongate side ports extending distally at an angle from the through bore,
    the pusher catheter further comprising two apertures near the distal end of the pusher catheter and the two apertures opening respectively into the two auxiliary lumens, the pusher catheter being in communication with the through bore of the manifold such that the two apertures communicate respectively with the two elongate side ports;
    an indwelling access sheath within each auxiliary lumen, the indwelling access sheaths each configured to receive a guide wire, the indwelling access sheaths extending through respective elongate side ports, into the manifold from external thereof, into the distal end of the stent graft, through the lumen of the stent graft, and out of respective fenestrations,
    wherein each of the two apertures of the pusher catheter comprises an elongate groove in the pusher catheter having a proximal end and a distal end and is tapered towards its distal end, and wherein each of the two apertures aligns with its respective elongate side port to provide an uninterrupted lumen from the respective elongate side port and through its respective auxiliary lumen.

2. The stent graft delivery device of claim 1, wherein each indwelling access sheath is configured to receive therethrough a further delivery device comprising a side arm stent.

3. The stent graft delivery device of claim 2, where the side arm stent is balloon expandable.

4. The stent graft delivery device of claim 1, wherein each side port has a haemostatic seal assembly and the respective access sheaths extend through the respective haemostatic seal assembly.

5. The stent graft delivery device of claim 1, wherein the stent graft has a scallop in the proximal end of the stent graft.

6. The stent graft delivery device of claim 1, further comprising a distally facing capsule at a distal end of the nose cone dilator, wherein the proximal end of the stent graft is releasably retained within the distally facing capsule.

7. The stent graft delivery device of claim 1, wherein the handle assembly comprises a proximal handle portion and a distal handle portion, the distal handle portion being movable longitudinally with respect to the proximal handle portion, the guide wire catheter extending through each of the distal handle portion and the proximal handle portion, the nose cone dilator and the distal handle portion being movable longitudinally with respect to the proximal handle portion whereby the nose cone dilator can be retracted or advanced independently of the manifold and pusher catheter.

8. The stent graft delivery device of claim 1, wherein the stent graft comprises a self-expanding stent structure.

9. A stent graft delivery device having two indwelling access sheaths preloaded with a stent graft on the delivery device, the stent graft delivery device comprising;
    a guide wire catheter having a guide wire lumen therethrough;
    a handle assembly at a distal end of the guide wire catheter, the handle including a multiport manifold;
    a nose cone dilator at the proximal end of the guide wire catheter, the nose cone dilator comprising a distally facing capsule on the distal end of the nose cone dilator;
    a pusher catheter extending from the manifold towards the nose cone dilator, the pusher catheter comprising a longitudinal pusher lumen therethrough that is offset from the center of the pusher catheter and two longitudinal auxiliary lumens, the pusher catheter completely enclosing the two longitudinal auxiliary lumens radially, a sheath disposed coaxially over the pusher catheter and the stent graft, the guide wire catheter extending through the pusher lumen and the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region;

the stent graft comprising a stent structure, graft material having a side wall, at least two fenestrations in the side wall of the graft material, a proximal end releasably retained within the distally facing capsule, a scallop in the proximal end of the graft, a distal end and a lumen therethrough;

the manifold comprising two elongate side ports and a through bore, the two elongate side ports extending distally at an angle from the through bore, the pusher catheter further comprising two apertures near the distal end of the pusher catheter and the two apertures opening respectively into the two auxiliary lumens, the pusher catheter being in communication with the through bore of the manifold such that the two apertures communicate respectively with the two elongate side ports;

an indwelling access sheath within each auxiliary lumen, the indwelling access sheaths each configured to receive a guide wire, the indwelling access sheaths extending through respective elongate side ports, into the manifold from external thereof, into the distal end of the stent graft, through the lumen of the stent graft, and out of respective fenestrations, wherein each of the two apertures of the pusher catheter comprises an elongate groove in the pusher catheter having a proximal end and a distal end and is tapered towards its distal end, and wherein each of the two apertures aligns with its respective elongate side port to provide an uninterrupted lumen from the respective elongate side port and through its respective auxiliary lumen.

10. The stent graft delivery device of claim 9, wherein each indwelling access sheath is configured to receive therethrough a further delivery device comprising a side arm stent.

11. The stent graft delivery device of claim 9, wherein each side port has a haemostatic seal assembly and the respective access sheaths extend through the respective haemostatic seal assembly.

12. A method of placing a fenestrated stent graft in a body vessel at a treatment site, comprising:

introducing a proximal end of a stent graft delivery device into a body vessel and advancing the delivery device to the treatment site, the stent graft delivery device comprising;

a guide wire catheter having a lumen therethrough;

a handle assembly at a distal end of the guide wire catheter, the handle including a multiport manifold;

a nose cone dilator at the proximal end of the guide wire catheter, the nose cone dilator comprising a distally facing capsule on the distal end of the nose cone dilator;

a pusher catheter extending from the manifold towards the nose cone dilator, the pusher catheter comprising a longitudinal pusher lumen therethrough that is offset from the center of the pusher catheter and two longitudinal auxiliary lumens, the pusher catheter completely enclosing the two longitudinal auxiliary lumens radially, a sheath disposed coaxially over the pusher catheter and the stent graft, the guide wire catheter extending through the pusher lumen and the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region;

the stent graft comprising a stent structure, graft material having a side wall, at least two fenestrations in the side wall of the graft material, a proximal end releasably retained within the distally facing capsule, a scallop in the proximal end of the graft, a distal end and a lumen therethrough;

the manifold comprising two elongate side ports and a through bore, the two elongate side ports extending distally at an angle from the through bore, the pusher catheter further comprising two apertures near the distal end of the pusher catheter and the two apertures opening respectively into the two auxiliary lumens, the pusher catheter being in communication with the through bore of the manifold such that the two apertures communicate respectively with the two elongate side ports;

an indwelling access sheath within each auxiliary lumen, the indwelling access sheaths each configured to receive a guide wire, the indwelling access sheaths extending through respective elongate side ports, into the manifold from external thereof, into the distal end of the stent graft, through the lumen of the stent graft, and out of respective fenestrations wherein each of the two apertures of the pusher catheter comprises an elongate groove in the pusher catheter having a proximal end and a distal end and is tapered towards its distal end, and wherein each of the two apertures aligns with its respective elongate side port to provide an uninterrupted lumen from the respective elongate side port and through its respective auxiliary lumen;

partially withdrawing the sheath from the stent graft to expose the indwelling access sheaths;

advancing a guide wire through each of the access sheaths, out of the respective fenestration and into a respective target branch vessel branching from the body vessel;

advancing the at least one access sheath to the target branch vessel;

releasing the proximal end of the stent graft from the distally facing capsule;

advancing a side arm stent through each of the indwelling access sheaths and at least partially out of the respective fenestration and into the respective target branch vessel, the side arm stents each having a proximal end and a distal end;

expanding each of the side arms within the target vessel with a balloon;

flaring the proximal ends of the side arm stents within the lumen of the stent graft.

13. A stent graft delivery device having two indwelling access sheaths preloaded with a stent graft on the delivery device, the stent graft delivery device comprising;

a guide wire catheter having a lumen therethrough;

a handle assembly at a distal end of the guide wire catheter, the handle including a multiport manifold;

a nose cone dilator at the proximal end of the guide wire catheter;

a pusher catheter extending from the manifold towards the nose cone dilator, the pusher catheter comprising a longitudinal pusher lumen therethrough and two longitudinal auxiliary lumens directly adjacent one another, the pusher catheter completely enclosing the two longitudinal auxiliary lumens radially, a sheath disposed coaxially over the pusher catheter and the stent graft, the guide wire catheter extending through the pusher lumen and the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region;

the stent graft comprising a stent structure, graft material having a side wall, at least two fenestrations in the side wall of graft material, a proximal end, a distal end and a lumen therethrough;

the manifold comprising two elongate side ports and a through bore, the two elongate side ports extending distally at an angle from the through bore, the pusher catheter further comprising two apertures near the distal end of the pusher catheter and the two apertures opening respectively into the two auxiliary lumens, the pusher catheter being in communication with the through bore of the manifold such that the two apertures communicate respectively with the two elongate side ports;

an indwelling access sheath within each auxiliary lumen, the indwelling access sheaths each configured to receive a guide wire, the indwelling access sheaths extending through respective elongate side ports, into the manifold from external thereof, into the distal end of the stent graft, through the lumen of the stent graft, and out of respective fenestrations, wherein each of the two apertures of the pusher catheter comprises an elongate groove in the pusher catheter having a proximal end and a distal end and is tapered towards its distal end, and wherein each of the two apertures aligns with its respective elongate side port to provide an uninterrupted lumen from the respective elongate side port and through its respective auxiliary lumen.

14. The stent graft delivery device of claim 13, wherein the pusher lumen is offset from the center of the pusher catheter.

15. The stent graft delivery device of claim 13, wherein the pusher lumen and the two longitudinal auxiliary lumens are arranged in cross-section to form a triangle.

16. A stent graft delivery device having two indwelling access sheaths preloaded with a stent graft on the delivery device, the stent graft delivery device comprising;

a guide wire catheter having a lumen therethrough;

a handle assembly at a distal end of the guide wire catheter, the handle including a multiport manifold;

a nose cone dilator at the proximal end of the guide wire catheter;

a pusher catheter extending from the manifold towards the nose cone dilator, the pusher catheter comprising a longitudinal pusher lumen therethrough and two longitudinal auxiliary lumens, the pusher catheter completely enclosing the two longitudinal auxiliary lumens radially, a sheath disposed coaxially over the pusher catheter and the stent graft, the guide wire catheter extending through the pusher lumen and the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region;

the stent graft comprising a stent structure, graft material having a side wall, at least two fenestrations in the side wall of graft material, a proximal end, a distal end and a lumen therethrough;

the manifold comprising two elongate side ports and a through bore, the two elongate side ports extending distally at an angle from the through bore, the pusher catheter further comprising two apertures near the distal end of the pusher catheter and the two apertures opening respectively into the two auxiliary lumens, the pusher catheter being in communication with the through bore of the manifold such that the two apertures communicate respectively with the two elongate side ports;

an indwelling access sheath within each auxiliary lumen, the indwelling access sheaths each configured to receive a guide wire and entering the pusher catheter proximal to the most distal end of the pusher catheter, the indwelling access sheaths extending through respective elongate side ports, into the manifold from external thereof, into the distal end of the stent graft, through the lumen of the stent graft, and out of respective fenestrations, wherein each of the two apertures of the pusher catheter comprises an elongate groove in the pusher catheter having a proximal end and a distal end and is tapered towards its distal end, and wherein each of the two apertures aligns with its respective elongate side port to provide an uninterrupted lumen from the respective elongate side port and through its respective auxiliary lumen.

17. A stent graft delivery device having two indwelling access sheaths preloaded with a stent graft on the delivery device, the stent graft delivery device comprising;

a guide wire catheter having a lumen therethrough;

a handle assembly at a distal end of the guide wire catheter, the handle including a multiport manifold disposed proximal to the distal end of the guide wire catheter;

a nose cone dilator at the proximal end of the guide wire catheter;

a pusher catheter extending from the manifold towards the nose cone dilator, the pusher catheter comprising a longitudinal pusher lumen therethrough and two longitudinal auxiliary lumens, the pusher catheter completely enclosing the two longitudinal auxiliary lumens radially, a sheath disposed coaxially over the pusher catheter and the stent graft, the guide wire catheter extending through the pusher lumen and the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region;

the stent graft comprising a stent structure, graft material having a side wall, at least two fenestrations in the side wall of graft material, a proximal end, a distal end and a lumen therethrough;

the manifold comprising two elongate side ports and a through bore, the two elongate side ports extending distally at an angle from the through bore, the pusher catheter further comprising two apertures near the distal end of the pusher catheter and the two apertures opening respectively into the two auxiliary lumens, the pusher catheter being in communication with the through bore of the manifold such that the two apertures communicate respectively with the two elongate side ports;

an indwelling access sheath within each auxiliary lumen, the indwelling access sheaths each configured to receive a guide wire, the indwelling access sheaths extending through respective elongate side ports, into the manifold from external thereof, into the distal end of the stent graft, through the lumen of the stent graft, and out of respective fenestrations, wherein each of the two apertures of the pusher catheter comprises an elongate groove in the pusher catheter having a proximal end and a distal end and is tapered towards its distal end, and wherein each of the two apertures aligns with its respective elongate side port to provide an uninterrupted lumen from the respective elongate side port and through its respective auxiliary lumen.

\* \* \* \* \*